US008551056B2

(12) United States Patent
Gagliardoni et al.

(10) Patent No.: US 8,551,056 B2
(45) Date of Patent: Oct. 8, 2013

(54) PINCH CLAMP ASSEMBLY FOR AN INFUSION CASSETTE

(75) Inventors: Giancarlo Gagliardoni, Estado Miranda (VE); Giuseppe Antonio Nichetti, Pandino (IT)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/379,199

(22) PCT Filed: Sep. 22, 2009

(86) PCT No.: PCT/EP2009/062292
§ 371 (c)(1),
(2), (4) Date: Feb. 3, 2012

(87) PCT Pub. No.: WO2010/149232
PCT Pub. Date: Dec. 29, 2010

(65) Prior Publication Data
US 2012/0136305 A1   May 31, 2012

(30) Foreign Application Priority Data

Jun. 25, 2009   (EP) .................. PCT/EP09/004601
Aug. 14, 2009   (EP) .................. PCT/EP09/060556

(51) Int. Cl.
*A61M 5/00*   (2006.01)

(52) U.S. Cl.
USPC ........................................ 604/250; 604/151

(58) Field of Classification Search
USPC .................. 604/151, 250–252, 255–256, 259
See application file for complete search history.

(56) References Cited

U.S. PATENT DOCUMENTS 4,635,092 A * 1/1987 Yerman et al. ................ 257/677
4,689,043 A   8/1987 Bisha
(Continued)

FOREIGN PATENT DOCUMENTS

TW   208167    6/1990
TW   1227148   10/2002
(Continued)

OTHER PUBLICATIONS

PCT International Search Report for International Application No. PCT/EP2009/062292 with a Mailing Date of Nov. 11, 2009, 3 pages.

*Primary Examiner* — Theodore J Stigell
*Assistant Examiner* — Melissa A Snyder
(74) *Attorney, Agent, or Firm* — K&L Gates LLP

(57) ABSTRACT

A pinch clamp assembly for engaging a tube (10) with an enteral feeding or infusion pump adapted to feed nutritionals or to infuse medical solutions to a patient, is provided comprising a base (1) comprising holding means (3) for holding a tube (10) in operative engagement with the base (1), a first clamping surface (4) and supporting means (5) for supporting a connector (6), a clamping element (7) having a second clamping surface (8) engageable with the tube (10) and moveable between an open position allowing flow of fluid through the tube (10) and a closed position wherein the tube (10) is occluded by the clamping element (7), a connector (6) for connecting the tube with a port on a patient, the connector (6) being removable from the pinch clamp assembly, and a spring (12), wherein the connector (6) is adapted to engage with the clamping element (7) so as to hold the clamping element (7) in the open position, wherein the clamping element (7) is forced from the open to the closed position by the force of the spring (12) as soon as the connector (6) is removed from the assembly, and wherein the clamping element (7) is adapted to be moved from the closed to the open position when the pinch clamp assembly is mounted to the enteral feeding or infusion pump and the connector (6) is removed.

15 Claims, 9 Drawing Sheets

(56) References Cited

U.S. PATENT DOCUMENTS

| | | | |
|---|---|---|---|
| 4,944,485 A | 7/1990 | Daoud et al. | |
| 7,070,575 B2 * | 7/2006 | Beck et al. | 604/67 |
| 2007/0265559 A1 | 11/2007 | Kunishige et al. | |

FOREIGN PATENT DOCUMENTS

| | | |
|---|---|---|
| WO | 9630679 | 10/1996 |
| WO | 03011377 | 2/2003 |

* cited by examiner

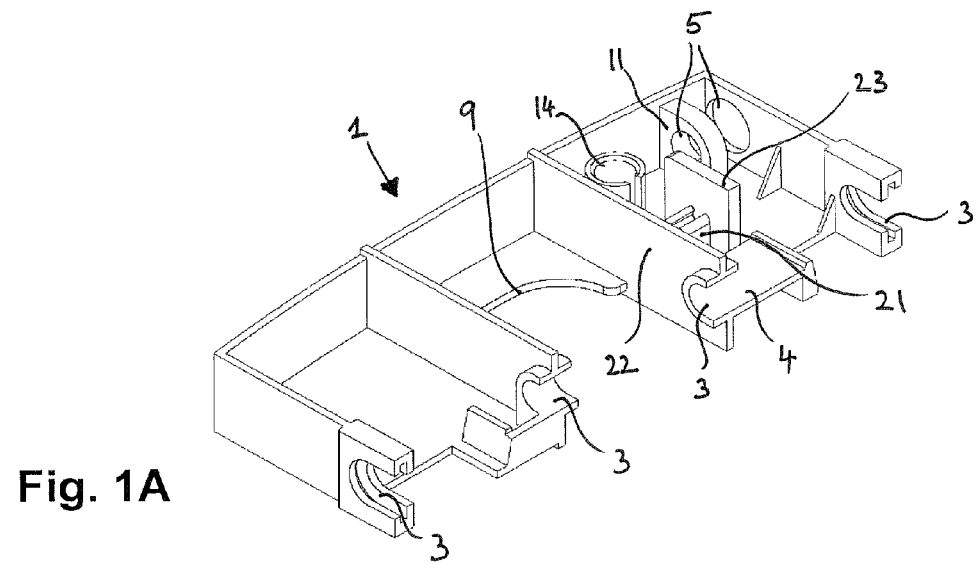
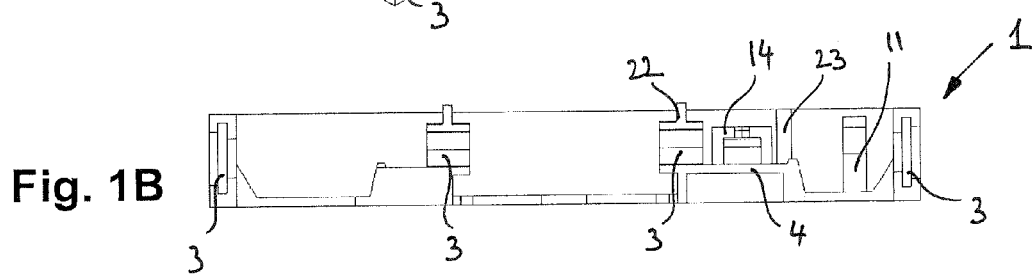
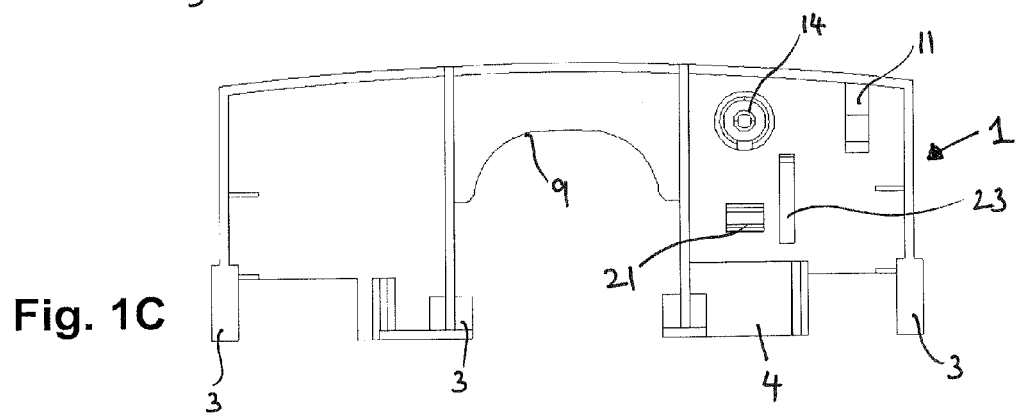
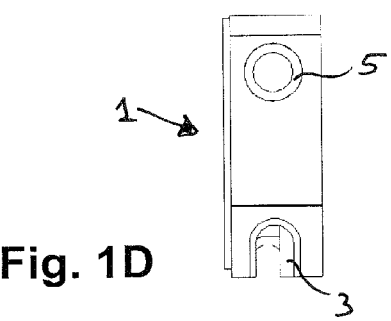

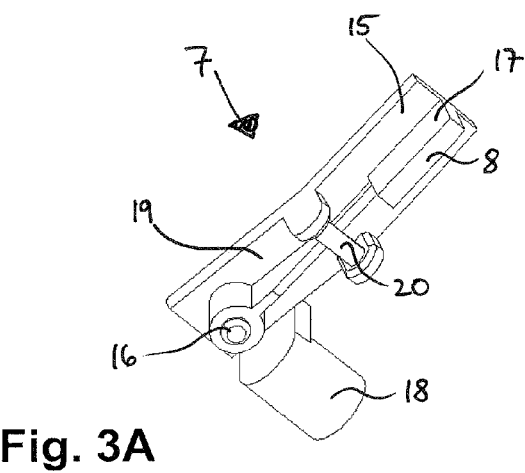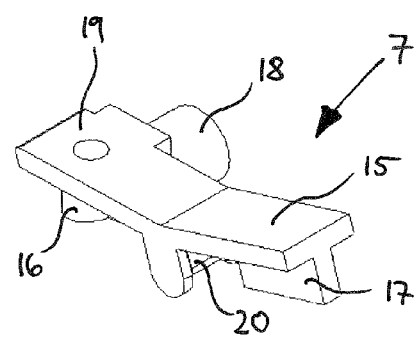
Fig. 3A       Fig. 3B
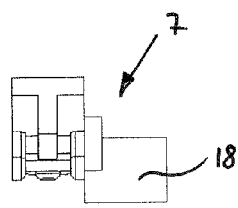
Fig. 3C
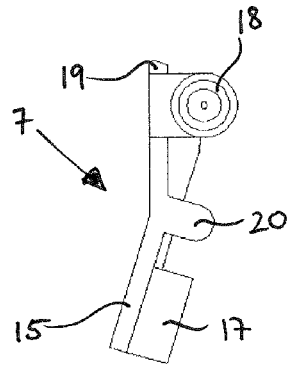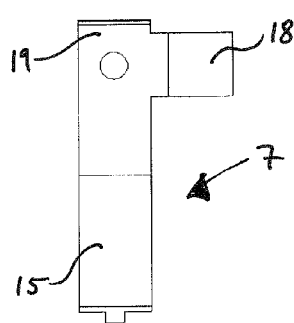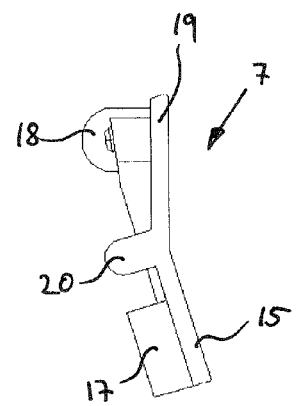
Fig. 3D       Fig. 3E       Fig. 3F

PINCH CLAMP ASSEMBLY FOR AN INFUSION CASSETTE

CROSS REFERENCE TO RELATED APPLICATIONS

The present application is a National Stage of International Application No. PCT/EP2009/062292, filed on Sep. 22, 2009, which claims priority to International Application No. PCT/EP2009/004601, filed on Jun. 25, 2009, and International Application No. PCT/EP2009/060556, filed Aug. 14, 2009, the entire contents of which are being incorporated herein by reference.

BACKGROUND OF THE INVENTION

The present invention relates to a pinch clamp assembly for engaging a tube with an enteral feeding pump adapted to feed nutritionals or an infusion pump adapted or to infuse medical solutions to a patient. More particularly, the present invention relates to a pinch clamp assembly in the form of a cassette with a clamping element for use on enteral feeding sets or infusion sets and the like, wherein the clamping element prevents the free-flow of enteral formula through the enteral feeding set or of solutions through the infusion set unless the clamping element together with the cassette are properly mounted in a housing or some other structure of an enteral feeding pump or infusion pump.

The use of infusion and feeding sets to administer solutions and food to a patient is well known in medical arts. Infusion and enteral sets are used for both enteral and parenteral application, respectively. For hygienic reasons the infusion and enteral sets must be disposed of immediately after use, making it single-use equipment which may be recycled afterwards. Enteral feeding pumps are used to provide the patient with nutrition and medication (formula) when they are unable, for a variety of reason, to eat normally. Parenteral (intravenous) solutions are provided to patients to ensure adequate hydration and to provide needed nutrients, minerals and medication. Often, the enteral or infusion set is placed in a free standing arrangement in which gravity forces the formula or solution into the patient. The rate at which the solution enters the patient can be roughly controlled by various clamps, such as roller clamps, which are currently available on the market.

In many applications, it is necessary to precisely control the amount of solution or formula which enters the patient. When this is the case, a regulating device such as an infusion pump, is placed along the infusion set to control the rate at which the solution is fed to the patient. In application where a pump etc. is used the clamps used to regulate flow are typically open to their fullest extent to prevent the clamp from interfering with the proper functioning of the pump. The clamp is opened with the expectation that the enteral feeding pump or infusion will control fluid flow through the enteral or infusion set. However, emergencies or other distractions may prevent the medical personnel from properly loading the enteral or infusion sets in the enteral feeding pump or the infusion pump. Furthermore, the enteral or infusion sets may be inadvertently dislodged from the pump during operation of the pump.

When the enteral or infusion set is not properly loaded in the pump and the clamp has been opened, a situation known as free-flow often develops. The force of gravity causes the solution or the formula to flow freely into the patient unchecked by the pump or other regulating device. Under a free-flow condition, an amount of solution or formula many times the desired dose can be supplied to the patient within a relatively short time period. This can be particularly dangerous if the solution contains potent medicine or the patient's body is not physically strong enough to adjust to the large inflow of solution or formula. Thus there is a need for a device that prevents a free-flow condition if the enteral or infusion set is not properly mounted in the pump or other regulation means. It is furthermore important that the device is tamper-resistant with regard to the generation of the free-flow condition. Another requirement for such enteral feeding or infusion sets is a long storage period which may be up to several years. Therefore a sticking and continuous deformation of the silicon tube is to be avoided which may result in a deviation of its regular flow properties when using it.

Several approaches have been taken to avoid the above mentioned free-flow situation one of which is disclosed in WO 96/030679 A1. Therein, a pinch clip occluder utilizes a clamping mechanism with at least one arm nested at least partially within a housing which serves as an adjustment mechanism by moving the arm between a position in which the arm occludes flow through an infusion set, and a position in which it allows free-flow through the infusion set. One problem related therewith is that the pinch clip occluder can still be manipulated in a way that the spring force may be countered by other external elements such as a squeeze, a fastener or the like. Another disadvantage of said infusion set including the pinch clip occluder is that mounting it to the infusion or enteral feeding pump is rather complicated, i.e. the silicon tube has to be positioned exactly in the recesses formed therefore and wrapped around the rotor unit etc. In addition, a major drawback of this known pinch clip occluder is that when the cap with the prone is left inside the pinch clip occluder to open the tube, a free-flow situation is caused even when the infusion set is not attached to the pump.

U.S. Pat. No. 4,689,043 describes an IV tube activator for use with a peristaltic IV infusion pump comprising means that require the closure of a tube associated clamp upon engagement of the IV tube with the pump and upon any subsequent disengagement of the IV tube from the pump. This IV tube activator also represents a rather complicated structure and will not solve the problem of storage of the clamped silicon tube before using it in the infusion pump. Furthermore, setting up the infusion set with the IV tube activator is cumbersome and error-prone due to the many different components.

SUMMARY OF THE INVENTION

It is therefore the object of the present invention to provide a pinch clamp assembly for engaging a tube with an enteral feeding or infusion pump adapted to feed nutritionals or to infuse medical solutions to a patient, which comprises a relatively simple construction, ensures an anti-free-flow mechanism that works at all times, and allows for a long time storage of the silicon tube.

This object is solved by the features of claim 1. Advantageous embodiments of the invention are subject of the subclaims.

According to the invention, a pinch clamp assembly for engaging a tube with an enteral feeding or infusion pump adapted to feed nutritionals or to infuse medical solutions to a patient comprises the following components: a base comprising holding means for holding a tube in operative engagement with the base, a first clamping surface and supporting means for supporting a connector, a clamping element having a second clamping surface engageable with the tube and moveable between an open position allowing flow of fluid through the tube and a closed position wherein the tube is occluded by the clamping element, a connector for connecting the tube with a port on a patient, the connector being removable from the pinch clamp assembly, and a spring, wherein the connector is adapted to engage with the clamping element so as to hold the clamping element in the open position, wherein the clamping element is forced from the open to the closed position by the force of the spring as soon as the connector is removed from the assembly, and wherein the clamping element is adapted to be moved from the closed to the open position when the pinch clamp assembly is mounted to the enteral feeding or infusion pump and the connector is removed.

Thereby, the free-flow condition is prevented when the pinch clamp assembly is in its delivery state because the connector which is to be connected to the port of the patient is still part of the pinch clamp assembly. As soon as the connector is removed the clamping element will automatically move to its closed position due to the force of the spring preventing any flow through the pumping section of the silicon tube. Therefore, the free-flow condition is again prevented when the respective connectors are connected to the port on the one end and to the solution or formula container on the other end. In this state, i.e. after the removal of the connector, the pinch clamp assembly may be inserted into the enteral feeding or infusion pump. When inserting the pump, the clamping element is opened due to the interaction of the pump with the clamping element. However, there is no free-flow condition because the pumping section of the silicon tube is so tightly wrapped around the pumping mechanism (rotor unit) of the enteral feeding or infusion pump that a flow of solution through the silicon tube is prevented. Thus, a free-flow condition of an infusion set comprising the pinch clamp assembly according to the present invention is avoided at all times, in particular before its first use.

Other advantages of the pinch clamp assembly according to the invention are that the assembly may be stored for a long time such as five years in its delivery state because the clamping element is in its open position and the silicon tube is not compressed or pinched thus preventing degradation or sticking of the material. Also the anti-free-flow mechanism is an integral part of the pinch clamp assembly avoiding any additional components.

The pinch clamp assembly of the present invention is also tamper-resistant because for a normal user it is impossible to close the clamping element with her or his hands when the connector is still inside the assembly. Only cutting the connector with its tip separated from the remainder might lead to the free-flow condition, however, this will inevitably destroy the function of the connector where both ends comprise special adapters that must fit other parts such as a port, luer lock or the like.

Preferably the clamping element is hinged at the base. This enables a rocker-like movement and mechanism and ensures the opening/closing interaction of the spring and the clamping element. A snap-in arrangement provides sufficient fixing to the clamping element.

In an advantageous embodiment the connector is an enteral spike, an IV (intravenous) spike, an enteral feeding adapter, an IV luer lock adapter or other enteral or IV component. All possible connectors known in the art of enteral feeding or infusion can be used.

It is preferred that the connector is threadedly coupled to the clamping element and/or the supporting means. This ensures that the connector is well fixed to the clamping element and prevents the connector from unintentionally falling out of the assembly. Other fixing means of the connector to the clamping element are also possible such as magnetic means, bayonet joint or the like.

In a preferred embodiment the base is formed as a cassette such that the pinch clamp assembly may be integrally mounted to the enteral feeding or infusion pump. A cassette provides a flat construction which is not bulky and yet comprises a compact format.

In a preferred embodiment the base, the clamping element and the connector are made of recyclable plastic material such as thermoplastics, the spring is made of metal and the pumping section of the tube is made of silicon or silicon replacement tubing. This enables a simple recycling procedure of this one-way and single-use equipment where only the spring is of a different material.

Preferably the base comprises a cylindrically-shaped holding element to accommodate spring. This ensures that the spring which is one of the core functional parts is constantly held at its place within the assembly.

In a preferred embodiment the clamping element comprises a first leg with a tube blocking portion, a second leg having means for engagement with the spring and a retainer for engagement with the connector, and a swivel pin adapted to engage with a suitable seating on base. The tube blocking portion ensures optimal interaction with the clamping surface of the base, the means for engagement with the spring ensure that the spring is kept at its designated functional place at all times, and the retainer ensures the engagement of the connector with the clamping element.

In another preferred embodiment the retainer is constructed as a cap or dust cover which is adapted to accommodate the tip of the connector. This enlarges the area of guidance for the connector and thus ensures the proper engagement of the connector with the clamping element. Furthermore it prevents dirt from getting into the opening of the connector. Also, a larger threaded area may be provided in such a cap and on the connector thus improving the engaging function.

In a preferred embodiment the clamping surfaces are uneven, corrugated or finned. Depending on the specific requirements of the silicon tubing, different set-ups of the clamping surfaces may be used.

It is preferred that the base comprises a first and a second inner wall between which clamping element is arranged. This ensures a good guidance of the clamping element perpendicular to the direction of the tube and avoids a potential access point for tampering to take out the clamping element.

According to another embodiment of the present invention an enteral feeding or infusion pump comprises a pinch clamp assembly as mentioned above, wherein the pump comprises releasing means adapted to engage with the clamping element so as to release the clamping element from the closed to the open position.

Preferably the flow through the pumping section is only enabled when the pinch clamp assembly is mounted. This ensures that the anti-free-flow mechanism is only disabled when the pinch clamp assembly is entirely mounted to the infusion pump.

BRIEF DESCRIPTION OF THE DRAWINGS

The above object, features and advantages of the present invention will become apparent from a consideration of the following detailed description presented in connection with the accompanying drawings in which:

FIG. 1A shows a perspective view of a cassette according to a preferred embodiment of the pinch clamp assembly according to the invention;

FIGS. 1B, 1C, 1D show a front view, plan view, and side view, respectively, of the cassette shown in FIG. 1A;

FIGS. 3A, 3B show perspective views of a clamping element according to a second embodiment of the pinch clamp assembly according to the invention;

FIGS. 3C, 3D, 3E, 3F show a front view, left side view, plan view, and right side view, respectively of the clamping element shown in FIGS. 3A and 3B;

DETAILED DESCRIPTION

Figure 2A:
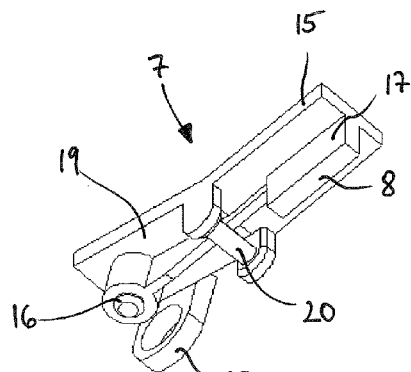
FIGS. 2A, 2B show perspective views of a clamping element according to a first embodiment of the pinch clamp assembly according to the invention.

FIG. 1A depicts a perspective view of the main component of a preferred embodiment of the pinch clamp assembly according to the invention which is comprised of cassette 1 forming the base of the assembly. Cassette 1 is configured generally rectangular and in a relatively flat structure. It is assumed that the cassette 1 is fabricated by injection moulding out of a thermoplastic material such as polypropylene, polystyrene, polyethylene or acrylnitrilbutadien-styrene (ABS), also other suitable thermoplastics may be used. Cassette 1 comprises four holding means 3 at opposing sides to support the pumping section of a silicon tube (not shown in this figure). Holding means 3 to accommodate the silicon tube are positioned towards the center and near the longitudinal edge of the cassette 1. Base or cassette 1 further comprises a first clamping surface 4 adjacent to holding means 3. First clamping surface 4 is flat and substantially parallel to the general plane of cassette 1. Its area is large enough to provide optimal clamping of the tube. Supporting means 5 are provided in cassette 1 in the form of a substantially round recess formed in a sidewall of the cassette 1 and a further substantially round recess formed in an inner wall 11 which is substantially parallel to the side wall which accommodates support 5. The substantially round recesses have substantially the same axis and are provided to support a connector which will be described in more detail later. Cassette 1 further comprises a cylindrically-shaped holding element 14 which is adapted to accommodate a spring as will be explained later. Parallel inner side walls 22 and 23 are formed substantially perpendicular to the direction of the tube. In addition a seating 21 is formed on the ground plate of cassette 1. In order not to over-complicate the figures with components not essential for the invention, the tube has been omitted at this point. The bottom portion of cassette 1 comprises a rotor unit recess 9. When mounting the pinch clamp assembly according to the invention to the enteral feeding or infusion pump the pins of the peristaltic rotor unit will fit into the space freed by the rotor unit recess 9. The claw-like contact area of holding means 3 is sufficiently large to provide a firm fit of the silicon tube.

FIGS. 1B, 1C and 1D are front, plan and side views of the pinch clamp assembly components of FIG. 1, wherein like numerals refer to like elements.

Figure 2B:
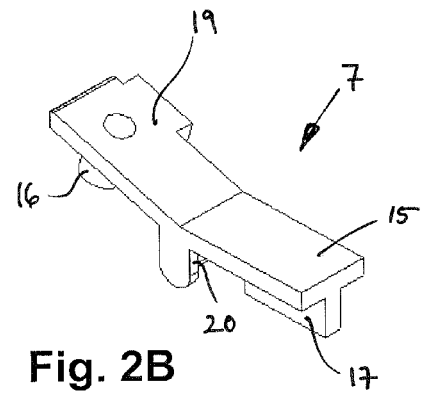
Figure 2C:
FIGS. 2C, 2D, 2E, 2F show a front view, left side view, plan view, and right side view, respectively, of the clamping element shown in FIGS. 2A and 2B.
Figure 2D:
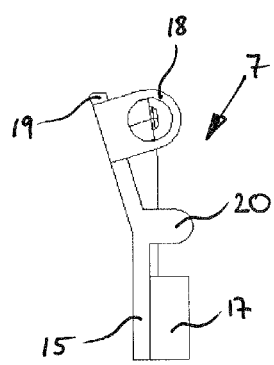
Figure 2E:
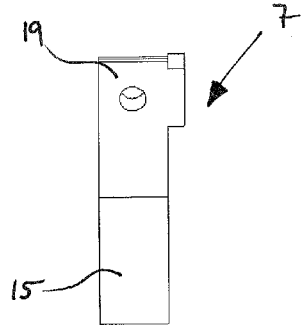
Figure 2F:
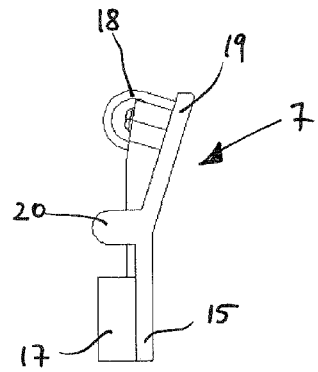

FIGS. 2A, 2B show perspective views of a clamping element 7 according to a first embodiment of the pinch clamp assembly according to the invention. Clamping element 7 is the central element of the pinch clamp assembly and is formed by first leg 15 with a tube blocking portion 17, a second leg 19 having means 16 for engagement with spring 12 (not shown) and a retainer 18 for engagement with connector 6. First leg 15 and second leg 19 stand against each other in an angle of approx. 10° to 20° so that a rocker-like setup is formed with a swivel pin 20 sitting in between. Swivel pin 20 is adapted to fit into the seating 21 formed in the cassette 1. Also, clamping element 7 is guided and enclosed between inner side walls 22 and 23. The tube blocking portion 17 comprises a second clamping surface 8 which is adapted to interact and engage with first clamping surface 4 of cassette 1. The means 16 are designed such that a perfect fit with spring 12 may be achieved. For stability purposes a T-bar like link between first leg 15, second leg 19, means 16 and tube blocking portion 17 is provided.

FIGS. 2C, 2D, 2E and 2F are front, left hand side, plan, and right hand side views, respectively of the clamping element shown in FIGS. 2A and 2B, wherein like numerals refer to like elements.

In the embodiment shown in FIGS. 2A to 2F the retainer 18 is formed substantially as a ring to accommodate the tip of connector 6. It must be noted that the connection between second leg 19 and retainer 18 should be very firm to ensure an optimal operation of the clamping element 7 as part of the pinch clamp assembly according to the invention.

FIGS. 3A, 3B show perspective views of a clamping element 7 according to a second embodiment of the pinch clamp assembly according to the invention. The difference between the first and the second embodiment is the form of retainer 18. In the second embodiment retainer 18 is formed as an elongated cylindrical cap or dust cover extending substantially perpendicular to the rocking direction clamping element 7. Enlarging the ring of retainer 18 of the first embodiment along its central axis will lead to the shape of retainer 18 of the second embodiment. It must be noted that shapes other than a cylindrical cap are possible. Also retainer 18 may comprise a flat surface on the inside or a thread. What is important is the interaction of retainer 18 with connector 6 as will be explained in detail later.

FIGS. 3C, 3D, 3E and 3F are front, left hand side, plan, and right hand side views, respectively of the clamping element shown in FIGS. 3A and 3B, wherein like numerals refer to like elements.

Figure 4:
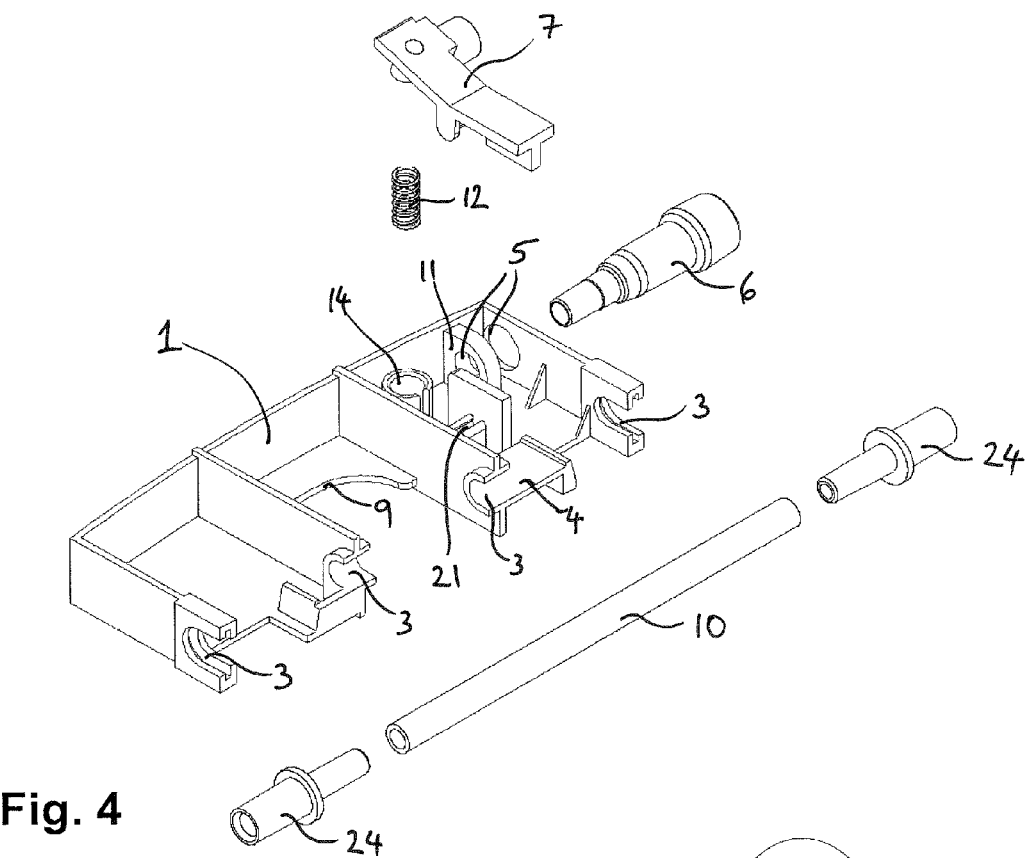
FIG. 4 shows a perspective exploded view of the second embodiment of the pinch clamp assembly according to the invention in a status before assembly of its components.
Figure 6:
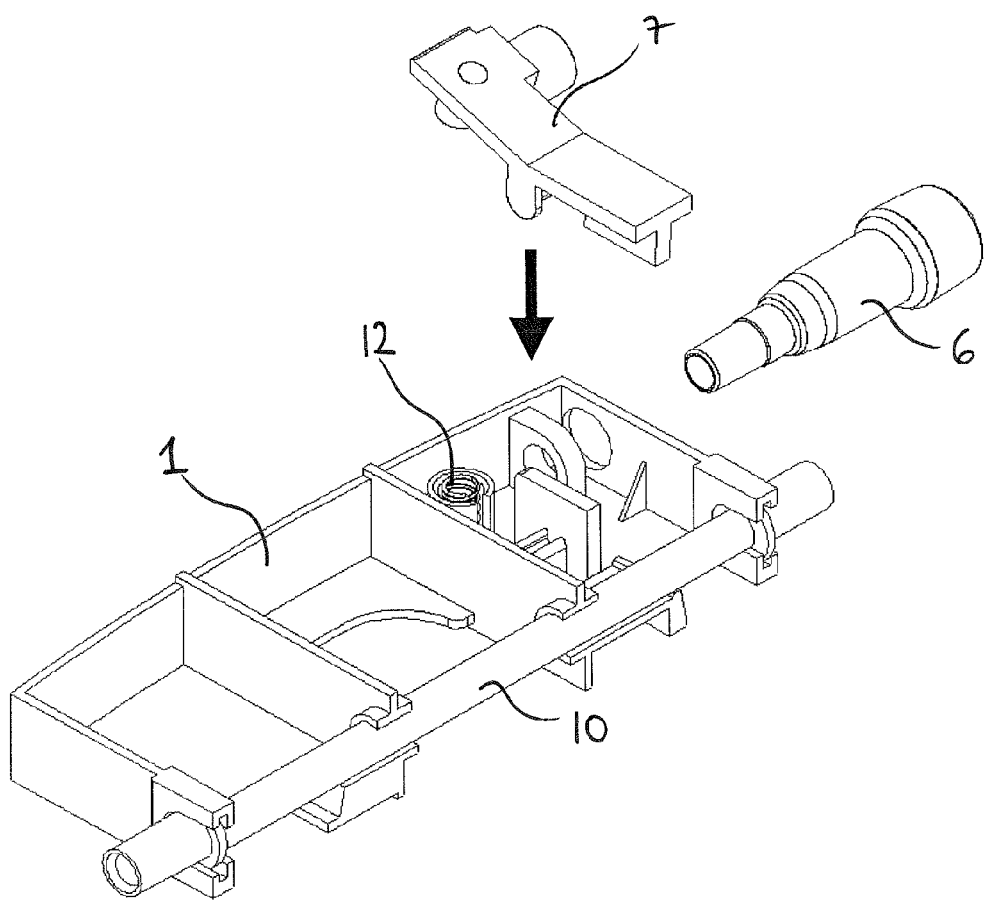
FIG. 6 shows a perspective exploded view of the second embodiment of the pinch clamp assembly according to the invention in a second mounting status.

FIG. 4 shows a perspective exploded view of the second embodiment of the pinch clamp assembly according to the invention in a status before assembly of its components. Tube 10 is comprised of a pumping section made of silicon or any other suitable material. On either end of tube 10 two tube fitting elements 24 are provided being adapted to hold silicon tube 10 and to fit into the holding means 3 provided at the longitudinal ends in the cassette 1 of the pinch clamp assembly. In order to provide a good fit the tube fitting elements 24 comprise a flange which is adapted to engage the recesses formed in the holding means 3 of cassette 1. FIG. 6 shows the tube 10 fitted into the pinch clamp assembly according to the invention. It is to be noted, that usually only the pumping section of the tubing portion of the entire infusion set is made of silicon, whereas the remaining portions of the tube are made of PVC (polyvinylchloride). Further it must be noted that the other components of an infusion set like the PVC tube are not depicted in the accompanying drawings as they do not contribute to the principle of the present invention.

Figure 5:
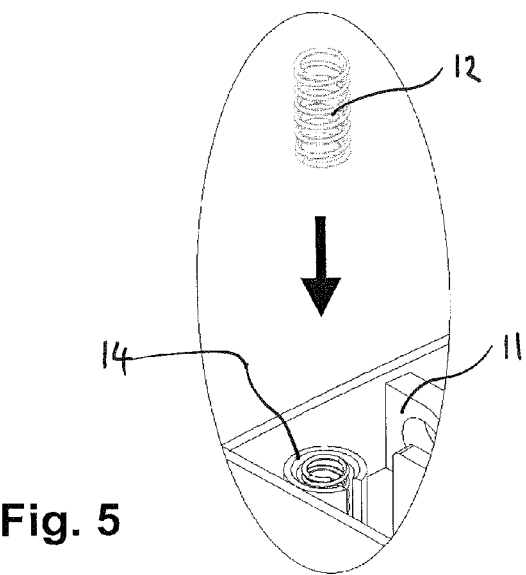
FIG. 5 shows a detail with spring of the pinch clamp assembly shown in FIG. 4.

Another key component of the pinch clamp assembly according to the invention is spring 12 which may be of metal or other suitable material with like characteristics. Before the clamping element 7 can be mounted to the cassette or base 1, the spring 12 must be inserted in the cylindrically-shaped holding element 14, as can be seen in detail in FIG. 5. Thereafter, the connector 6 which in the shown embodiment is an enteral adapter may be mounted to the assembly together with the clamping element 7 (see FIG. 6). The swivel pin 20 of clamping element 7 must be inserted in the seating 21 of cassette 1 against the force of the spring 12. Thereby, the tube 10 will be compressed between the first and second clamping surfaces 4 and 8 on base 1 and the tube blocking portion 17 of clamping element 7. In the shown embodiment the clamping surfaces of the tube blocking portion 17 and the second leg 19 are flat. However, it is possible that the clamping surfaces are uneven, corrugated or finned so as to facilitate the squeezing function of the clamping element 7 depending on the characteristics of the silicon tube.

Figure 7:
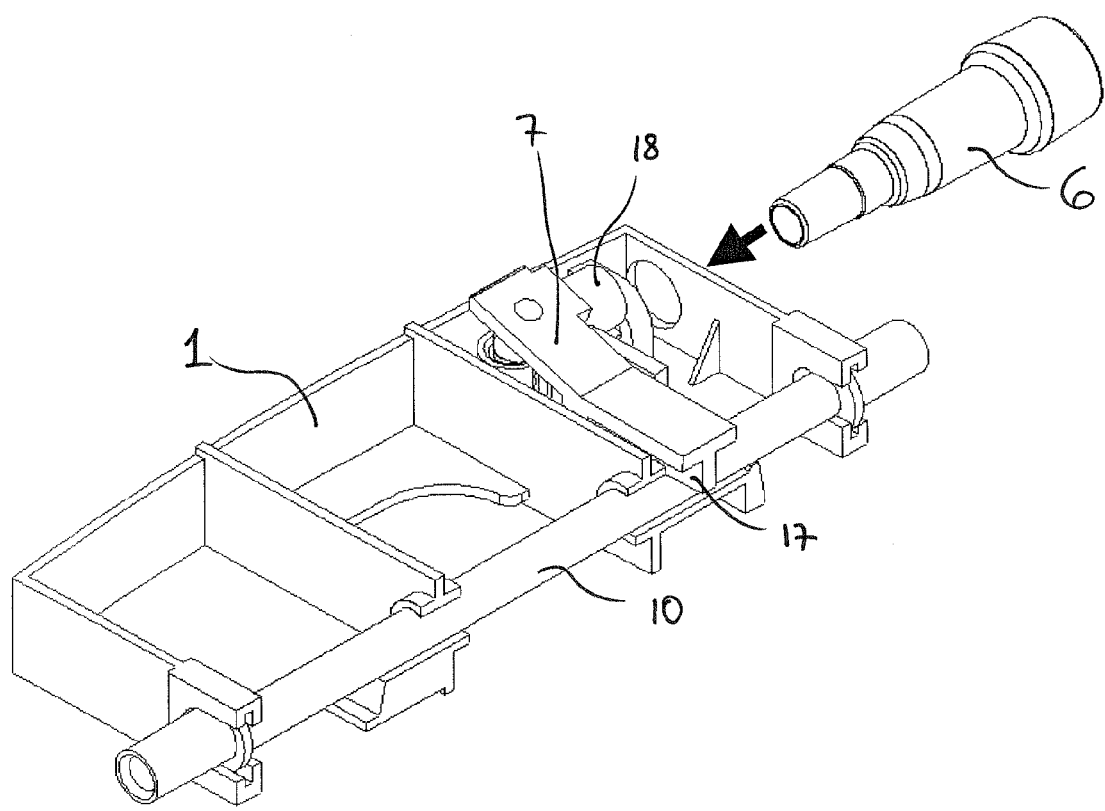
FIG. 7 shows a perspective exploded view of the second embodiment of the pinch clamp assembly according to the invention in a third mounting status.

According to the object of the present invention the tube must not be compressed during the delivery status of the pinch clamp assembly. Therefore, the clamping element 7 must somehow be tilted such that the clamping surfaces stay apart. This is achieved by holding down the clamping element 7 on the second leg 19 so that the spring 12 is compressed with one end in the cylindrically-shaped holding element 14 and the other end on means 16. Then, in the lowest position of the second leg 19, i.e. when means 16 substantially touch the cylindrically-shaped holding element 14, the connector 6 which is meanwhile inserted through the supports 5 in the side wall and in the inner wall 11 of cassette 1 (see FIG. 7), is moved along its axis further with its tip such that it is inserted into the retainer or cap 18 of clamping element 7. Retainer or cap 18 is in this second embodiment formed as a cylinder which is closed on the clamping element side thus preventing dust to enter the connector 6 when in engagement. This engagement serves as a locking mechanism keeping the clamping element 7 down on the side of the second leg 19 which in turn means that the first leg 15 is kept on top such that the first and second clamping surfaces 4 and 8 are apart and thus freeing tube 10. This position where the tube 10 is open and the clamping element 7 is held down against the force of the spring 12 is called the open position.

Figure 8:
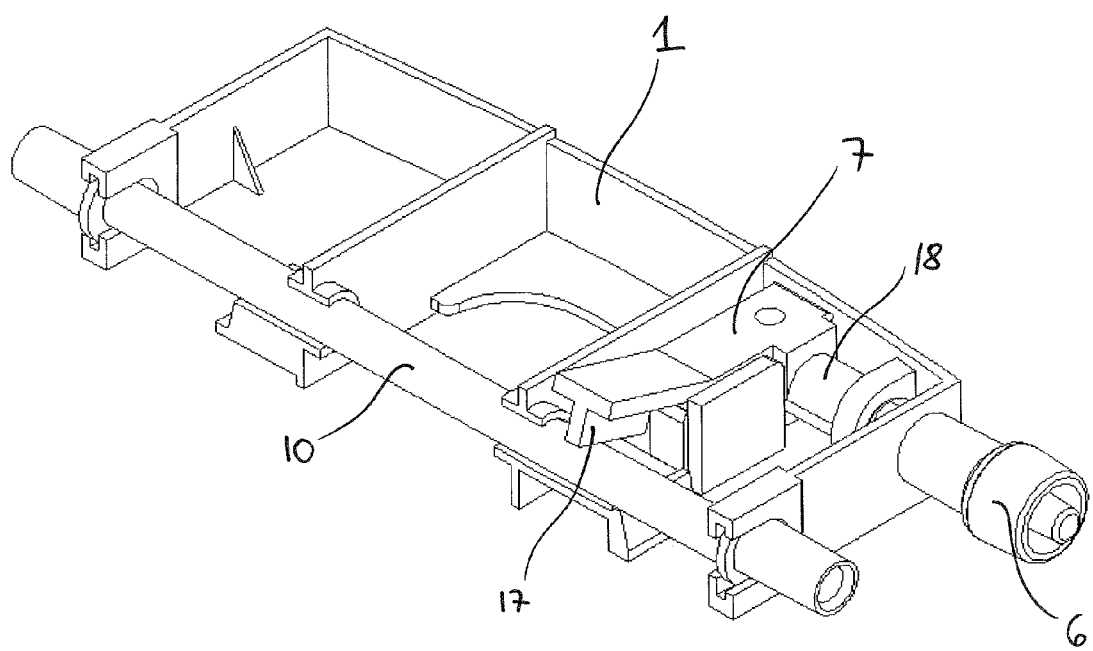
FIG. 8 shows a perspective view of the second embodiment of the pinch clamp assembly according to the invention in delivery status.
Figure 9A:
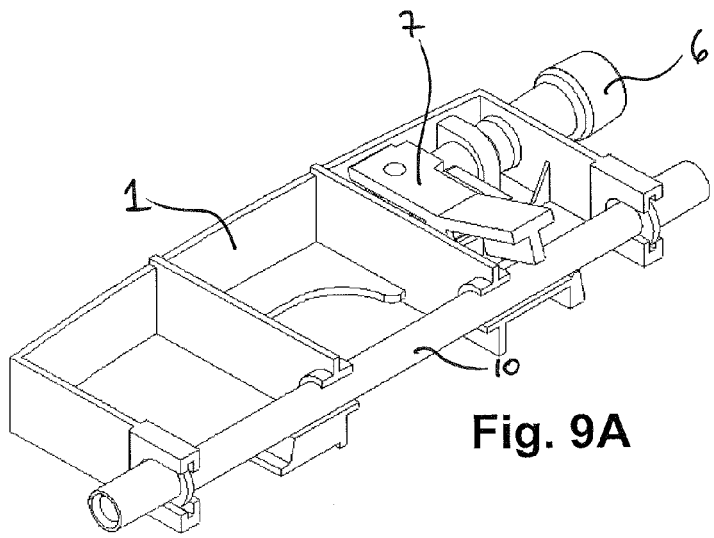
FIGS. 9A, 9B show the pinch clamp assembly of FIG. 8 in different perspective views.
Figure 9B:
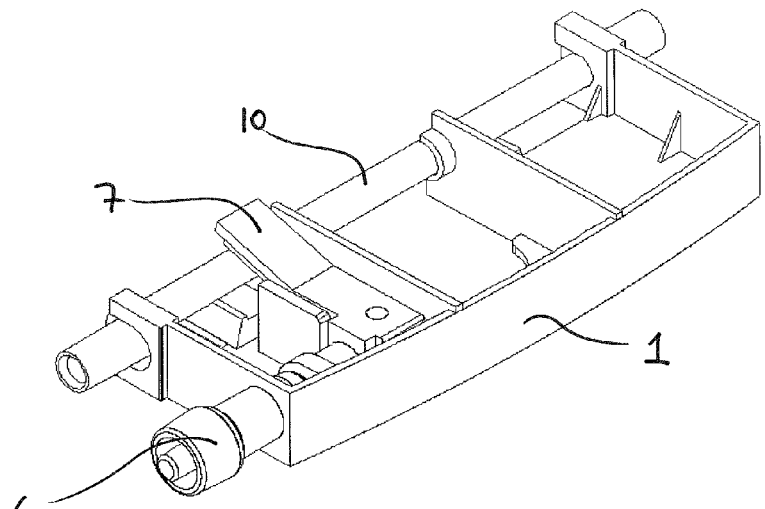

FIGS. 8, 9A and 9B show the second embodiment of the pinch clamp assembly according to the invention in the open position, viewed from different sides. It must be noted that the connector 6 is firmly engaged with the retainer 18 such that it cannot fall out of the assembly without pulling in axial direction. The Figs. show as connector 6 an enteral adapter which on one end comprises a tapered fit. It is to be noted that other types of connectors may be used and that the connector 6 is on its outwardly directing end directly connected to a tube, e.g. via solvent bonding. Also, luer type locks may be used for connecting to a tube.

The engagement between the connector 6 and the retainer 18 and/or the supports 5 in the sidewall of the cassette 1 and the inner wall 11 may be improved by providing a thread on the opposing surfaces. This is especially preferable in the shown second embodiment where the retainer 18 is formed as cap or dust cover.

As stated before the open position with the connector 6 mounted in the pinch clamp assembly represents the delivery status. In order to mount the pinch clamp assembly in an enteral feeding or infusion pump the connector 6 must be removed from the assembly, must be mounted to the port of the patient, and the assembly without connector 6 must be inserted into the corresponding slot in the pump.

As soon as the connector 6 is removed from the pinch clamp assembly, the clamping element 7 will go to the closed position thereby blocking the flow through the tube 10. Removing the connector 6 means moving the tip of the connector away from its engagement with retainer 18 (cap/dust cover or ring). This disengagement releases the spring 12 which will push against the means 16 of clamping element 7 and move the second leg 19 up. In turn, this will lead to an immediate closure of the tube 10 as the clamping surfaces 4 and 8 are pressed against each other with the silicon tube 10 in between. The clamping element 7 thus serves a tilting switch opening and closing the flow through the tube 10 depending on the status of the spring 12. The closed position can be seen in FIGS. 10A and 10B showing different perspective views of the second embodiment of the pinch clamp assembly according to the invention.

It is the key principle of the present invention that while connector 6 is firmly engaged in and thus integral part of the pinch clamp assembly, the assembly is in delivery state and in open position. It is not possible to generate a free flow condition since the connector 6 is held tightly within the assembly and removing the connector 6 from the assembly will immediately bring the clamping element 7 to its closed position. Thus the flow through the silicon tube 10 is always occluded before inserting the pinch clamp assembly into the pump.

Figure 10A:
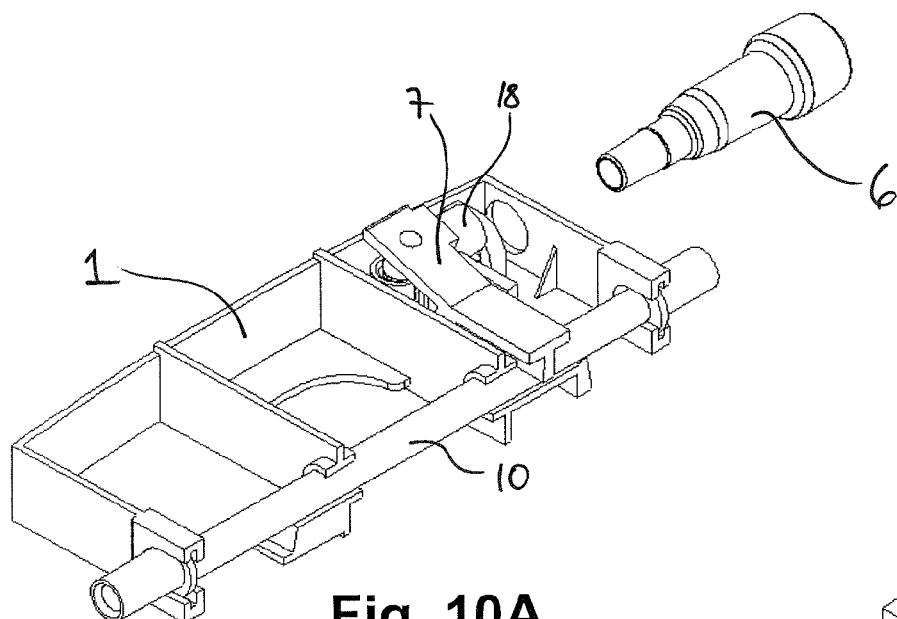
FIGS. 10A, 10B show perspective views of the second embodiment of the pinch clamp assembly according to the invention with the clamping element removed.
Figure 10B:
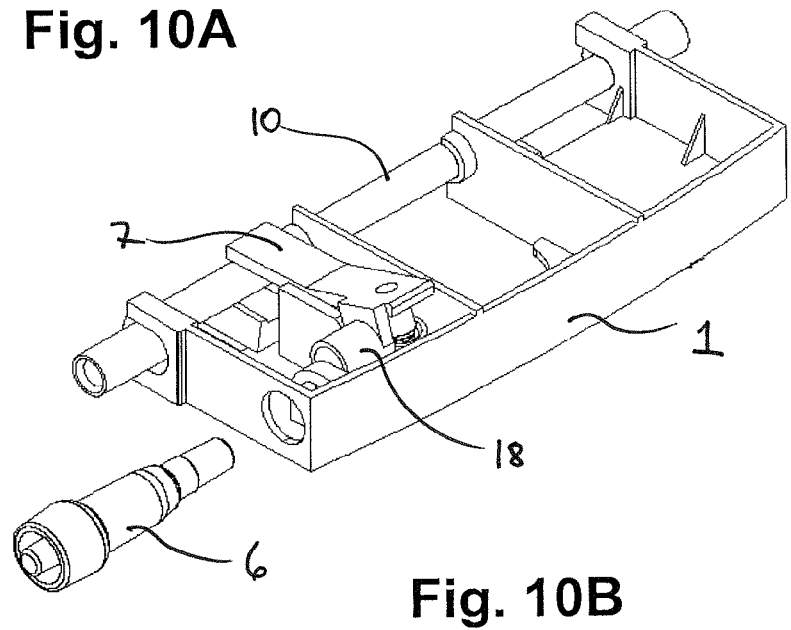

It is to be noted that the pinch clamp assembly as shown in FIGS. 10A and 10B is adapted to be mounted to an enteral feeding or infusion pump as is. Of course before the mounting can take place, connector 6 has to be removed. When mounting the pinch clamp assembly, with connector 6 removed, to the enteral feeding or infusion pump the clamping element 7 is still in its closed position thereby occluding the flow of liquid through the pumping section of silicon tube 10. The free flow condition is thus avoided. However, the occluded status of the pumping section of the silicon tube 10 must be released as soon as the cassette 1 with the other components of the pinch clamp assembly is inserted into the enteral feeding or infusion pump. From FIGS. 10A and 10B it can be seen that the second leg 19 protrudes with its upper surface from the upper surface of the rest of the assembly. Therefore, the pump comprises releasing means that will press down the second leg 19 of the clamping element 7 against the force of the spring 12 thus bringing the clamping surfaces 4 and 8 apart so as to open the flow through the tube 10. The person skilled in the art will contemplate a variety of designs for the pump in order to press down the second leg 19 of the clamping element 7.

In the above preferred embodiment a locking and releasing mechanism has been described. It is to be noted, that other locking-releasing mechanisms are possible such as a magnetic solution or a solution with fastening means. All alternative solutions however should fulfil the central requirement which is that they are tamper-resistant so that the clamping element 7 cannot be opened easily by hand or with tools which are easily available to medical personnel without the connector 6 removed.

With the subject-matter of the present invention a pinch clamp assembly for engaging a tube with an enteral feeding or an infusion pump adapted to feed nutritionals or to infuse medical solutions to a patient has been provided which comprises a relatively simply construction, ensures an anti-free-flow mechanism that works at all times, and allows for a long time storage of the silicon tube.

The invention claimed is:

1. A pinch clamp assembly for engaging a tube with an enteral feeding or infusion pump adapted to provide solutions to a patient, the pinch clamp assembly comprising:
   a base comprising a holder for holding a tube in operative engagement with the base, a first clamping surface and a support for supporting a connector;
   a clamping element having a second clamping surface engageable with the tube and moveable between an open position allowing the flow of fluid through the tube and a closed position wherein the tube is occluded by the clamping element;
   a connector for connecting the tube with a port on a patient, the connector being removable from the pinch clamp assembly;
   a spring;
   the connector is adapted to engage with the clamping element so as to hold the clamping element in the open position;
   the clamping element is forced from the open to the closed position by the force of the spring as soon as the connector is removed from the assembly; and
   the clamping element is adapted to be moved from the closed to the open position when the pinch clamp assembly is mounted to the pump and the connector is removed.

2. The pinch clamp assembly of claim 1, wherein the base is formed as a cassette such that the pinch clamp assembly may be integrally mounted to the pump.

3. The pinch clamp assembly of claim 1, wherein the base comprises a cylindrically-shaped holding element to accommodate the spring.

4. An enteral feeding pump comprising:
   a pinch clamp assembly for engaging a tube with an enteral feeding or infusion pump adapted to provide solutions to a patient, the pinch clamp assembly comprising: a base comprising a holder for holding a tube in operative engagement with the base, a first clamping surface and a support for supporting a connector, a clamping element having a second clamping surface engageable with the tube and moveable between an open position allowing flow of fluid through the tube and a closed position wherein the tube is occluded by the clamping element, a connector for connecting the tube with a port on a patient, the connector being removable from the pinch clamp assembly, a spring, the connector is adapted to engage with the clamping element so as to hold the clamping element in the open position, the clamping element is forced from the open to the closed position by the force of the spring as soon as the connector is removed from the assembly, and the clamping element is adapted to be moved from the closed to the open position when the pinch clamp assembly is mounted to the pump and the connector is removed; and
   comprising a release element adapted to engage with clamping element.

5. An infusion pump comprising:
   a pinch clamp assembly for engaging a tube with an enteral feeding or infusion pump adapted to provide solutions to a patient, the pinch clamp assembly comprising: a base comprising a holder for holding a tube in operative engagement with the base, a first clamping surface and a support for supporting a connector, a clamping element having a second clamping surface engageable with the tube and moveable between an open position allowing flow of fluid through the tube and a closed position wherein the tube is occluded by the clamping element, a connector for connecting the tube with a port on a patient, the connector being removable from the pinch clamp assembly, a spring, the connector is adapted to engage with the clamping element so as to hold the clamping element in the open position, the clamping element is forced from the open to the closed position by the force of the spring as soon as the connector is removed from the assembly, and the clamping element is adapted to be moved from the closed to the open position when the pinch clamp assembly is mounted to the pump and the connector is removed; and
   a release element adapted to engage with the clamping element.

6. A pinch clamp assembly for engaging a tube with an enteral feeding or infusion pump adapted to provide solutions to a patient, the pinch clamp assembly comprising:
   a base comprising a holder for holding a tube in operative engagement with the base, a first clamping surface and a support for supporting a connector;
   a clamping element having a second clamping surface engageable with the tube and moveable between an open position allowing the flow of fluid through the tube and a closed position wherein the tube is occluded by the clamping element;
   a connector for connecting the tube with a port on a patient, the connector being removable from the pinch clamp assembly;
   a spring;
   the connector is adapted to engage with the clamping element so as to hold the clamping element in the open position;
   the clamping element is forced from the open to the closed position by the force of the spring as soon as the connector is removed from the assembly; and
   the clamping element is hinged at the base and is adapted to be moved from the closed to the open position when the pinch clamp assembly is mounted to the pump and the connector is removed.

7. A pinch clamp assembly for engaging a tube with an enteral feeding or infusion pump adapted to provide solutions to a patient, the pinch clamp assembly comprising:
   a base comprising a holder for holding a tube in operative engagement with the base, a first clamping surface and a support for supporting a connector;
   a clamping element having a second clamping surface engageable with the tube and moveable between an open position allowing the flow of fluid through the tube and a closed position wherein the tube is occluded by the clamping element;
   a connector for connecting the tube with a port on a patient, the connector being removable from the pinch clamp assembly, and selected from the group consisting of an enteral spike, an IV spike, an enteral feeding adapter, and an IV luer lock adapter;
   a spring;
   the connector is adapted to engage with the clamping element so as to hold the clamping element in the open position;

the clamping element is forced from the open to the closed position by the force of the spring as soon as the connector is removed from the assembly; and the clamping element is adapted to be moved from the closed to the open position when the pinch clamp assembly is mounted to the pump and the connector is removed.

8. A pinch clamp assembly for engaging a tube with an enteral feeding or infusion pump adapted to provide solutions to a patient, the pinch clamp assembly comprising:

a base comprising a holder for holding a tube in operative engagement with the base, a first clamping surface and a support for supporting a connector;

a clamping element having a second clamping surface engageable with the tube and moveable between an open position allowing the flow of fluid through the tube and a closed position wherein the tube is occluded by the clamping element;

a connector for connecting the tube with a port on a patient, the connector being removable from the pinch clamp assembly;

a spring;

the connector is threadedly coupled to the clamping element and/or the support, and adapted to engage with the clamping element so as to hold the clamping element in the open position;

the clamping element is forced from the open to the closed position by the force of the spring as soon as the connector is removed from the assembly; and the clamping element is adapted to be moved from the closed to the open position when the pinch clamp assembly is mounted to the pump and the connector is removed.

9. A pinch clamp assembly for engaging a tube with an enteral feeding or infusion pump adapted to provide solutions to a patient, the pinch clamp assembly comprising:

a base comprising a holder for holding a tube in operative engagement with the base, a first clamping surface and a support for supporting a connector;

a clamping element having a second clamping surface engageable with the tube and moveable between an open position allowing the flow of fluid through the tube and a closed position wherein the tube is occluded by the clamping element;

a connector for connecting the tube with a port on a patient, the connector being removable from the pinch clamp assembly;

a spring;

the base, the clamping element and the connector are made of recyclable plastic material, the spring is made of metal, and the tube is made of silicon;

the connector is adapted to engage with the clamping element so as to hold the clamping element in the open position;

the clamping element is forced from the open to the closed position by the force of the spring as soon as the connector is removed from the assembly; and the clamping element is adapted to be moved from the closed to the open position when the pinch clamp assembly is mounted to the pump and the connector is removed.

10. A pinch clamp assembly for engaging a tube with an enteral feeding or infusion pump adapted to provide solutions to a patient, the pinch clamp assembly comprising:

a base comprising a holder for holding a tube in operative engagement with the base, a first clamping surface and a support for supporting a connector;

a clamping element having a second clamping surface engageable with the tube and moveable between an open position allowing the flow of fluid through the tube and a closed position wherein the tube is occluded by the clamping element;

a connector for connecting the tube with a port on a patient, the connector (6) being removable from the pinch clamp assembly;

a spring;

the connector is adapted to engage with the clamping element so as to hold the clamping element in the open position;

the clamping element comprises a first leg with a tube blocking portion, a second leg for engagement with the spring and a retainer for engagement with the connector, and a swivel pin adapted to engage with a suitable seat of the base;

the clamping element is forced from the open to the closed position by the force of the spring as soon as the connector is removed from the assembly; and the clamping element is adapted to be moved from the closed to the open position when the pinch clamp assembly is mounted to the pump and the connector is removed.

11. The pinch clamp assembly of claim 10, wherein the retainer is constructed as a cap which is adapted to accommodate the tip of the connector.

12. A pinch clamp assembly for engaging a tube with an enteral feeding or infusion pump adapted to provide solutions to a patient, the pinch clamp assembly comprising:

a base comprising a holder for holding a tube in operative engagement with the base, a first clamping surface and a support for supporting a connector;

a clamping element having a second clamping surface engageable with the tube and moveable between an open position allowing the flow of fluid through the tube and a closed position wherein the tube is occluded by the clamping element, wherein first and/or second clamping surfaces have a structure selected from the group consisting of uneven, corrugated and finned;

a connector for connecting the tube with a port on a patient, the connector (6) being removable from the pinch clamp assembly;

a spring;

the connector is adapted to engage with the clamping element so as to hold the clamping element in the open position;

the clamping element is forced from the open to the closed position by the force of the spring as soon as the connector is removed from the assembly; and the clamping element is adapted to be moved from the closed to the open position when the pinch clamp assembly is mounted to the pump and the connector is removed.

13. A pinch clamp assembly for engaging a tube with an enteral feeding or infusion pump adapted to provide solutions to a patient, the pinch clamp assembly comprising:

a base comprising a holder for holding a tube in operative engagement with the base, a first clamping surface and a support for supporting a connector;

a clamping element having a second clamping surface engageable with the tube and moveable between an open position allowing the flow of fluid through the tube and a closed position wherein the tube is occluded by the clamping element, wherein the base comprises a first and a second inner wall between which the clamping element is located;

a connector for connecting the tube with a port on a patient, the connector (6) being removable from the pinch clamp assembly;

a spring;

the connector is adapted to engage with the clamping element so as to hold the clamping element in the open position;

the clamping element is forced from the open to the closed position by the force of the spring as soon as the connector is removed from the assembly; and the clamping element is adapted to be moved from the closed to the open position when the pinch clamp assembly is mounted to the pump and the connector is removed.

14. An enteral feeding pump comprising:

a pinch clamp assembly for engaging a tube with an enteral feeding or infusion pump adapted to provide solutions to a patient, the pinch clamp assembly comprising:

a base comprising a holder for holding a tube in operative engagement with the base, a first clamping surface and a support for supporting a connector, a clamping element having a second clamping surface engageable with the tube and moveable between an open position allowing flow of fluid through the tube and a closed position wherein the tube is occluded by the clamping element, a connector for connecting the tube with a port on a patient, the connector being removable from the pinch clamp assembly, a spring, the connector is adapted to engage with the clamping element so as to hold the clamping element in the open position, the clamping element is forced from the open to the closed position by the force of the spring as soon as the connector is removed from the assembly, and the clamping element is adapted to be moved from the closed to the open position when the pinch clamp assembly is mounted to the pump and the connector is removed; and comprising a release element adapted to engage with clamping element, wherein the flow through the tube is only enabled when the pinch clamp assembly is mounted thereon.

15. An infusion pump comprising:

a pinch clamp assembly for engaging a tube with an enteral feeding or infusion pump adapted to provide solutions to a patient, the pinch clamp assembly comprising:

a base comprising a holder for holding a tube in operative engagement with the base, a first clamping surface and a support for supporting a connector, a clamping element having a second clamping surface engageable with the tube and moveable between an open position allowing flow of fluid through the tube and a closed position wherein the tube is occluded by the clamping element, a connector for connecting the tube with a port on a patient, the connector (6) being removable from the pinch clamp assembly, a spring, the connector is adapted to engage with the clamping element so as to hold the clamping element in the open position, the clamping element is forced from the open to the closed position by the force of the spring as soon as the connector is removed from the assembly, and the clamping element is adapted to be moved from the closed to the open position when the pinch clamp assembly is mounted to the pump and the connector is removed; and a release element adapted to engage with the clamping element, wherein flow through the tube is only enabled when the pinch clamp assembly is mounted thereon.

* * * * *